United States Patent
Heo et al.

(10) Patent No.: US 11,642,318 B2
(45) Date of Patent: May 9, 2023

(54) COMPOSITION COMPRISING LACTIC ACID BACTERIA IMPROVED IN INTESTINAL ADHERENCE BY COATING WITH SILK FIBROIN

(71) Applicant: CKD Bio Corp., Seoul (KR)

(72) Inventors: Bohye Heo, Gyeonggi-do (KR); Youil Kim, Gwangju (KR); Woolee Kim, Incheon (KR); Minho Seo, Gyeonggi-do (KR); Byoungkook Kim, Seoul (KR); Insuk Choi, Gyeonggi-do (KR)

(73) Assignee: CKD Bio Corp., Seoul (KR)

( * ) Notice: Subject to any disclaimer, the term of this patent is extended or adjusted under 35 U.S.C. 154(b) by 641 days.

(21) Appl. No.: 16/500,952

(22) PCT Filed: Apr. 5, 2018

(86) PCT No.: PCT/KR2018/004026
§ 371 (c)(1),
(2) Date: Oct. 4, 2019

(87) PCT Pub. No.: WO2018/186700
PCT Pub. Date: Oct. 11, 2018

(65) Prior Publication Data
US 2021/0121410 A1    Apr. 29, 2021

(30) Foreign Application Priority Data
Apr. 7, 2017    (KR) .................. 10-2017-0045326

(51) Int. Cl.
*A61K 9/00*    (2006.01)
*A61K 9/50*    (2006.01)
(Continued)

(52) U.S. Cl.
CPC .......... *A61K 9/5052* (2013.01); *A61K 9/5042* (2013.01); *A61K 35/744* (2013.01);
(Continued)

(58) Field of Classification Search
CPC .................................................. A61K 9/5052
See application file for complete search history.

(56) References Cited

U.S. PATENT DOCUMENTS

2015/0164117 A1    6/2015  Kaplan et al.

FOREIGN PATENT DOCUMENTS

| KR | 10-2002-0069862 | 9/2002 |
| KR | 10-2009-0029528 A | 3/2009 |

(Continued)

OTHER PUBLICATIONS

Extended European Search Report from corresponding European Patent Application No. 18781131.0, dated Feb. 24, 2020.
(Continued)

*Primary Examiner* — Benjamin J Packard
(74) *Attorney, Agent, or Firm* — Harness, Dickey & Pierce, P.L.C.

(57) ABSTRACT

The present invention relates to a method for improving lactic acid bacteria in survival rate, storage stability, resistance to acid or bile, and adherence to intestinal epithelial cells by coating the surface of lactic acid bacteria with silk fibroin, and a lactic acid bacteria composition prepared therethrough. Conventional techniques construct only a physical protective barrier outside a lactic acid bacteria body by multi-stage coating and thus retain the limitation of being unable to identify an effect on the coherence of lactic acid bacteria to intestinal epithelial cells upon the uptake of the lactic acid bacteria. In contrast, the present invention provides a method in which lactic acid bacteria is coated with silk fibroin extracted from cocoons, whereby the lactic acid
(Continued)

bacteria is improved in stability under a storage and distribution condition as well as having remarkably increased stability and intestinal adherence particularly under an intestinal environment.

8 Claims, 7 Drawing Sheets

(51) Int. Cl.

| | | |
|---|---|---|
| *A61P 1/00* | (2006.01) | |
| *A61K 35/744* | (2015.01) | |
| *A61K 35/745* | (2015.01) | |
| *A61K 35/747* | (2015.01) | |
| *C12N 1/20* | (2006.01) | |
| *C12N 11/02* | (2006.01) | |
| *C12N 11/12* | (2006.01) | |
| *A61K 35/00* | (2006.01) | |

(52) U.S. Cl.
CPC .......... *A61K 35/745* (2013.01); *A61K 35/747* (2013.01); *A61P 1/00* (2018.01); *C12N 1/20* (2013.01); *C12N 11/02* (2013.01); *C12N 11/12* (2013.01); *A61K 2035/115* (2013.01); *C12N 2500/14* (2013.01)

(56) References Cited

FOREIGN PATENT DOCUMENTS

| KR | 10-2010-0005976 | 1/2010 |
|---|---|---|
| KR | 10-2012-0046676 A | 5/2012 |
| KR | 10-2013-0070111 | 6/2013 |
| KR | 10-1605516 | 3/2016 |

OTHER PUBLICATIONS

Yildirim, S., et al.; "Development of silk fibroin-based beads for immobilized cell fermentations", Journal of Microencapsulation, 2010, 27(1), pp. 1-9.

Li, Ling, et al.; "Investigation of the physiochemical properties, cryoprotective activity and possible action mechanisms of sericin peptides derived from membrane separation", LWT-Food Science and Technology, 77, 2017, pp. 532-541.

Coghetto, C. C., et al.; "Probiotics production and alternative encapsulation methodologies to improve their viabilities under adverse environmental conditions", International Journal of Food Sciences and Nutrition, 67:8, pp. 929-943.

Solanki, H. K., et al.; "Development of Microencapsulation Delivery System for Long-Term Preservation of Probiotics as Biotherapeutics Agent", BioMed Research International, 2013, 21 pages.

Huq, T., et al.; "Encapsulation of Probiotic Bacteria in Biopolymeric System", Critical Reviews in Food Science and Nutrition, 53:9, 2013, pp. 909-916.

Jiménez-Pranteda, M. L., et al.; "Stability of lactobacilli encapsulated in various microbial polymers", Journal of Bioscience and Bioengineering, vol. 113, No. 2, 2012, pp. 179-184.

International Search Report from corresponding PCT Application No. PCT/KR2018/004026, dated Aug. 9, 2018.

Biowave, 2009, vol. 11, No. 7, pp. 1-20.

Shah, N. P., et al.; "Functional culturesand health benefits", International Dairy Journal, 17 (2007) pp. 1262-1277.

Talwalkar, A., et al.; A Review of Oxygen Toxicity in Probiotic Yogurts: Influence on the Survival of Probiotic Bacteria and Protective Techniques, Comprehensive Reviews in Food Science and Food Safety, vol. 3, 2004, pp. 117-124.

Talwalkar A., et al.; "The Role of Oxygen in the Viability of Probiotic Bacteria with Reference to L. acidophilus and *Bifidobacterium* spp.", Curr. Issues Intest. Microbiol. (2004) 5: 1-8.

Alconada, T. M., et al.; "Purification and characterization of a βglucosidase from the phytopathogenic fungus *Fusarium oxysporum* f. sp. *melonis*", Letters in Applied Microbiology, 1996, 22, pp. 106-110.

Tripathi, M. K., et al.; "Probiotic functional foods: Survival of probiotics during processing and storage", Journal of Functional Foods, 9, 2014, pp. 225-241.

Kailasapathy, K et al.; "Survival and therapeutic potential of probiotic organisms with reference to Lactobacillus acidophilus and *Bifidobacterium* spp." Immunology and Cell Biology (2000) 78, 80-88.

Tuomola, E., et al.; Quality assurance criteria for probiotic bacteria1-4, Am J Clin Nutr 2001;73(suppl):393S-8S.

Forssten, S. D., et al.; "Chapter 2 The Intestinal Microbiota and Probiotics", *Probiotic Bacteria and Enteric Infections*,2011, pp. 41-63.

Jin, H., et al.; "Mechanism of silk processing in insects and spiders", Letters to Nature, vol. 424, Aug. 28, 2003, pp. 1057-1061.

BioWave, vol. 9, No. 7, 2007, pp. 1-11.

Blum, S., et al.; "Adhesion studies for probiotics: need for validation and refinement", Trends in Food Science & Technology 10 (1999) 405-410.

Lee, K., et al; "Probiotic Effects of Lactobacillus plantarum and Leuconostoc mesenteroides Isolated from Kimchi", J Korean Soc Food Sci Nutr, 45(1), 12?19(2016).

Xu, M.; "Development of protein-based hydrogels as encapsulatin matrices for Lactobacillus casei ATTC 393" A theses submitted to McGill University for the degree of Master of Science, 2015, pp. 1-98.

Del Re, B., et al; "Autoaggregation and adhesion ability in a Bifidobacterium suis strain", Letters in Applied Microbiology, 1998,27, 307-310.

Office Action from corresponding Chinese Patent Application No. 201880023718.9, dated Jan. 22, 2021.

Control group (uncoated)
 Test group 1
 Test group 2
 Test group 3

COMPOSITION COMPRISING LACTIC ACID BACTERIA IMPROVED IN INTESTINAL ADHERENCE BY COATING WITH SILK FIBROIN

CROSS-REFERENCE TO RELATED APPLICATIONS

This application is a national phase application of PCT Application No. PCT/KR2018/004026, filed on Apr. 5, 2018, which claims priority to Korean Patent Application No. 10-2017-0045326, filed on Apr. 7, 2017. The entire disclosures of the applications identified in this paragraph are incorporated herein by reference.

FIELD

The present invention was made with the support of the Rural Development Administration of the Republic of Korea, under Project No. PJ01128701, which was conducted in the research project titled "Next-Generation BioGreen 21" within the project named "Development of industrial manufacturing process of health functional food material with cholesterol lowering effect" by ChongKunDang Bio Co., Ltd. under the management of the Rural Development Administration, from 15 Jan. 2015 to 31 Dec. 2017.

The present invention relates to a method for improving viability, storage stability, resistance against acid or bile, and intestinal epithelial cell adhesion of lactic acid bacteria by coating the surface of the lactic acid bacteria with silk fibroin, and to a lactic acid bacteria composition manufactured thereby.

BACKGROUND

Lactic acid bacteria are a group of bacteria that produce lactic acid by using sugars as energy sources. Lactic acid bacteria are found in the human or mammalian digestive tract, oral cavity, and vagina, and are widely distributed in natural systems, such as various types of fermented foods. Lactic acid bacteria are one group of the microorganisms that have been widely utilized for the longest time by mankind. Lactic acid bacteria are microorganisms that produce no harmful substances in the human or animal intestines and have a beneficial function of preventing decay in the intestines.

Lactic acid bacterial are currently classified into 12 genera (*Lactobacillus, Carnobacterium, Atopobium, Lactococcus, Pediococcus, Tetragenococcus, Leuconostoc, Weissella, Oenococcus, Enterococcus, Streptococcus*, and *Vagococcus*). The usually used lactic acid bacteria are the rod-shaped bacterium (*Lactobacillus* sp.), the sphere-shaped bacteria (*Lactococcus* sp., *Streptococcus* sp., *Leuconostoc* sp., and *Pediococcus* sp.), and the like (BioWave, 2009, Vol. 11, No. 7, pp. 1-20).

Meanwhile, probiotics are defined as living microorganisms, which when administered in adequate amounts, confer a benefit on the host, or as a food containing the living microorganism (FAO/WHO 2001), and help to maintain and control human intestinal microorganism at normal levels. The representative probiotics are lactic acid bacteria and *Bifidobacterium* bacteria, and besides, yeasts (*Saccharomyces cerevisiae* and *Saccharomyces boulardii*), filamentous fungus (*Aspergillus oryzae*), and the like are included in probiotics.

Representative effects of probiotics have been known to include antibacterial activity, alleviation of antibiotic-related diarrhea, reduction of lactose intolerance, anti-cancer effects, lowering of blood cholesterol, inhibition of *Helicobacter pylori* bacteria in the stomach, alleviation of irritable colitis, Crohn's disease, and ulcerative colitis, immune function regulation, and the like (International Dairy Journal, 2007, Vol. 17, pp. 1262-1277). Probiotics may be divided into intestinal drugs or lactic acid bacteria preparations as human medicines, probiotics as feed additives, and lactic acid bacterial foods as a kind of health food. The lactic acid bacteria foods refers to foods that are mixed with viable cells of *Lactobacillus, Lactococcus, Bifidobacterium*, or the like, and are manufactured into a powder, granules, a tablet, a capsule, and the like to be stable and easy to ingest.

The manufacturing processes for such lactic acid bacteria foods are divided into culture of lactic acid bacteria, cell recovery, freeze-drying, disruption, productization, and the like. The lactic acid bacteria are exposed to various types of physical and chemical stresses during the manufacturing processes of lactic acid bacteria foods. Specifically, the lactic acid bacteria are affected by the osmotic pressure due to the concentration during cell recovery, and are simultaneously affected by the osmotic pressure and the temperature due to ice crystallization and dehydration during freeze-drying. The lactic acid bacteria may also be exposed to high temperatures and high pressures during disruption and productization, and may be exposed to air to cause the oxidation of lipids constituting cellular membranes, resulting in a decrease in survival rate (Comprehensive Reviews in Food Science and Food Safety, 2004, Vol. 3, pp. 117-124; Curr. Issues Intest. Microbiol., 2004, Vol. 5, pp. 1-8; Letters in Applied Microbiology, 1996, Vol. 22, No. 1, pp. 3438).

In addition, the exposure of lactic acid probiotics to high temperatures and humidity and aerobic conditions during storage or distribution greatly affects the survival and growth of the probiotics (Journal of Functional Foods, 2014, Vol. 9, pp. 225-241).

Unlike the other industrial microorganism-fermented products, probiotic products use viable cells and thus are exposed to various types of stresses in the human body before reaching the intestines after ingestion. For example, the probiotic products are exposed to a strong acid environment of about pH 2 and various digestive enzymes in the stomach, and are affected by digestive enzymes and bile acids secreted into the small intestine when reaching the small intestine. Furthermore, the ingested lactic acid probiotics undergo growth inhibition due to various harmful components and reactive oxygen species in the intestines even though the probiotics reach the intestines, and simultaneously, the probiotics need to adhere to intestinal epithelial cells while competing with existing various microorganisms settling in the intestine (Immunology and Cell Biology, 2000, Vol. 78, pp. 8088; American Journal of Clinical Nutrition (AJCN), 2001, Vol. 73, pp. 393S398S (suppl); Probiotic Bacteria and Enteric Infections, 2011, Chap. 2, pp. 41-63).

There is therefore an urgent need for solutions to minimize not only the reduction of stability of probiotics due to an environment, such as osmotic pressure, temperature, pressure, humidity, or exposure to air, in manufacturing, storing, and distributing conditions of lactic acid bacteria, but also the cell death by stresses caused by exposure to intestinal environments after ingestion, and to solve the growth inhibition of cells in the intestines.

In order to solve the above problems, various methods for coating lactic acid bacteria have been developed. In early days, enteric coating agents using capsules and microcapsulation using gelatin, polysaccharides, gums, and the_ like were developed. However, the above methods have problems of using high-priced coating agents or adding processes. To solve the problems, a method for manufacturing double-structured jellies with high concentrations of lactic acid bacteria or a double coating method using a protein and a polysaccharide was introduced (Korean Patent Application No. 10-2003-0020375 and Korean Patent Application No. 10-2001-0010397) or a triple-coating method using nanoparticles in combination with protein and polysaccharide coating was introduced (Korean Patent Publication No. 10-2008-0008267). However, such lactic acid bacteria coating techniques had a problem that lactic acid bacteria were still not sufficiently excellent in resistance against heat, acid, and bile since the surfaces of the lactic acid bacteria were not completely coated. Also, multi-coating using edible oil in combination with triple coating (Korean Patent Application No. 10-2011-0093074), quadruple coating through addition of a water-soluble polymer, hyaluronic acid, a coating agent having porous particles, and a protein (Korean Patent Application No. 10-2011-0134486), and the like were competitively developed, but these lactic acid bacteria coating techniques required a multi-step process of recovering lactic acid bacteria cells cultured by an ordinary method, mixing the lactic acid bacteria cells with coating compositions, and stirring the mixture, and thus these techniques made it difficult to perform aseptic manipulation of probiotics and especially caused a deterioration in economical efficiency in view of industrial mass production. Korean Patent Registration No. 10-1605516 suggested an effective method capable of enhancing storage stability and resistance against acid and bile of products by adopting the addition of proline during a manufacturing process, but such suggestion could not confirm an effect associated with intestinal epithelial cell adhesion, which can be exerted by lactic acid bacteria reaching the small intestine or large intestine after ingestion. In order to solve the problems, the present inventors endeavored to develop a method for enhancing intestinal epithelial cell adhesion of lactic acid bacteria to be capable of not only improving stability of the manufactured lactic acid probiotics in processing and distribution conditions but also maximizing biological activity of the lactic acid probiotics in intestine tract environments after ingestion.

Throughout the present specification, reference is made to many papers and patent documents and the citations thereof are provided. The disclosure of the cited papers and patent documents is incorporated in the present specification by reference in their entirety to describe the level of the technical field to which the present invention pertains and the contents of the present invention more clearly.

SUMMARY

Technical Problem

An aspect of the present invention is to provide a composition containing lactic acid bacteria coated with silk fibroin.

Another aspect of the present invention is to provide a composition containing lactic acid bacteria coated with silk fibroin and cellulose.

A still another aspect of the present invention is to provide a method for promoting the culture of lactic acid bacteria, the method including culturing lactic acid bacteria in a medium supplemented with silk fibroin.

Still another aspect of the present invention is to provide a method for enhancing viability, storage stability, resistance against acid or bile, and intestinal epithelial cell adhesion of lactic acid bacteria.

Other purposes and advantages of the present invention will be clarified by the following detailed description of the invention, claims, and drawings.

Technical Solution

The present invention provides the following compositions or methods.

1. A composition comprising lactic acid bacteria coated with silk fibroin.
2. The composition of 1., wherein the lactic acid bacteria are coated with silk fibroin and cellulose.
3. The composition of 1. and 2., wherein the silk fibroin is pre-treated with ethanol.
4. The composition of 3., wherein the ethanol has a concentration of 85% (v/v) or more.
5. The composition of 1. to 4., wherein the lactic acid bacteria are selected from the group consisting of the genera *Lactobacillus, Lactococcus, Enterococcus, Streptococcus,* and *Bifidobacterium*.
6. The composition of 1. to 5., wherein the lactic add bacteria are selected from the group consisting of *Lactobacillus acidophilus, Lactobacillus plantarum, Lactobacillus delbrueckii* ssp. *bulgaricus, Lactococcus lactis, Enterococcus faecium, Enterococcus faecalis, Streptococcus thermophilus, Bifidobacterium bifidum,* and *Bifidobacterium lactis*.
7. The composition of 1. to 6., wherein the lactic add bacteria are selected from the group consisting of *Lactobacillus acidophilus* CKDB007 (Accession No.: KCTC13117BP), *Enterococcus faecium* CKDB003 (Accession No.: KCTC13115BP), *Streptococcus thermophilus* CKDB021 (Accession No.: KCTC13118BP), *Bifidobacterium bifidum* CKDB001 (Accession No.: KCTC13114BP), and *Bifidobacterium lactis* CKDB005 (Accession No.: KCTC13116BP).
8. The composition of 1. to 7., wherein the composition is selected from the group consisting of a food composition, a probiotic composition, a pharmaceutical composition, and a feed composition.
9. A method for promoting the culture of lactic acid bacteria, the method comprising culturing lactic acid bacteria in a medium supplemented with silk fibroin.
10. A method for manufacturing lactic acid probiotics coated with silk fibroin, the method comprising culturing lactic acid bacteria in a medium containing silk fibroin for culturing lactic acid bacteria.
11. The method of 10., wherein the medium for culturing lactic acid bacteria further contains water-soluble calcium.
12. The method of 11., wherein the water-soluble calcium is added at a concentration of 0.01-5% (w/v) relative to the volume of the medium for culturing lactic acid bacteria.
13. The method of 10. to 12., wherein the medium for culturing lactic acid bacteria further contains cellulose.
14. A method for enhancing viability, storage stability, resistance against acid or bile, and intestinal epithelial cell adhesion of lactic acid bacteria, the method comprising culturing the lactic acid bacteria in a medium containing silk fibroin for culturing lactic acid bacteria.
15. The method of 9., 10., or 14., wherein the medium supplemented with silk fibroin or the medium containing silk fibroin for culturing lactic acid bacteria further contains water-soluble calcium.

16. The method of 15., wherein the water-soluble calcium is added at a concentration of 0.01-5 wt % relative to the volume of the medium for culturing lactic acid bacteria.

17. The method of 14., wherein the medium for culturing lactic acid bacteria further contains cellulose.

18. The method of 10. to 17., wherein the lactic acid bacteria are selected from the group consisting of the genera *Lactobacillus, Lactococcus, Enterococcus, Streptococcus*, and *Bifidobacterium*.

19. The method of 10. to 18., wherein the lactic acid bacteria are selected from the group consisting of *Lactobacillus acidophilus, Lactobacillus plantarum, Lactobacillus delbrueckii* ssp. *bulgaricus, Lactococcus lactis, Enterococcus faecium, Enterococcus fecalis, Streptococcus thermophilus, Bifidobactedum bifidum*, and *Bifidobacterium lactis*.

20. The method of 10. to 19., wherein the lactic acid bacteria are selected from the group consisting of *Lactobacillus acidophilus* CKDB007 (Accession No.: KCTC13117BP), *Enterococcus faecium* CKDB003 (Accession No.: KCTC13115BP), *Streptococcus thermophilus* CKDB021 (Accession No.: KCTC13118BP), *Bifidobacterium bifidum* CKDB001 (Accession No.: KCTC13114BP), and *Bifidobacterium lactis* CKDB005 (Accession No.: KCTC13116BP).

21. A method for enhancing viability, storage stability, resistance against acid or bile, and intestinal epithelial cell adhesion of lactic acid bacteria, the method comprising culturing the lactic acid bacteria in a medium containing silk fibroin for culturing lactic acid bacteria.

In accordance with an aspect of the present invention, there is provided a composition containing lactic acid bacteria coated with silk fibroin.

In accordance with another aspect of the present invention, there is provided a composition containing lactic acid bacteria coated with silk fibroin and cellulose.

The present invention verified that the addition of silk fibroin during the culture of lactic acid bacteria promoted the culture of lactic acid bacteria, thereby shortening the culture time of the lactic acid bacteria, and additionally verified that the addition of silk fibroin during or after the culture of lactic acid bacteria improved the viability in freeze-drying and stability in severe conditions.

The present inventors also verified that after the completion of the culture of lactic acid bacteria, the cultured cells were recovered and then the lactic acid bacteria cells were coated with silk fibroin optimized in various treatment conditions, and as a result, the lactic acid bacteria were greatly enhanced in resistance against acid and bile, which are resistance indicators to stresses, and were significantly enhanced in intestinal epithelial cell adhesion.

As used herein, the term "silk fibroin" refers to an amino acid composite organic substance prepared by living silkworms through extrusion. Silk fibroin has a molecular weight of about 84,000 g/mol, and contains the amino acids glycine, alanine, and serine distributed at a ratio of 3:2:1, which account for 70-80% of all the amino acids. In addition, tyrosine, valine, aspartate, glutamate, and the other amino acids account for about 13% of all the amino acids. Such silk fibroin has been approved by the FDA, and widely used in various fields, such as surgical sutures, drug carriers, histological use, burn treatment, and enzyme immobilization.

According to an embodiment of the present invention, the silk fibroin may be prepared from silkworms by acid hydrolysis or enzymatic hydrolysis, but any method that is ordinarily used to prepare silk fibroin in the art can be employed without limitation.

According to another embodiment of the present invention, the silk fibroin may be pre-treated with 85% (v/v) or more ethanol. Here, the 85% or more ethanol is specifically fermented ethanol. According to the liquor tax law, the fermented ethanol is obtained by fermenting starch-containing materials or sugar-containing materials, followed by distillation to an alcohol content of 85 degrees or more, wherein the fermented ethanol is prepared by feeding a diastatic enzyme to a starch (cereals, sweet potatoes, tapioca) or sugar (candy-) raw material, followed by fermentation and then distillation in a continuous distillation manner, and the fermented ethanol is used as a raw material for manufacturing diluted soju.

Many proteins have α-helix and β-sheet sites in a single polypeptide chain. Silk fibroin is also composed of two types, silk I and silk II types, and silk I type has an α-helix structure and silk II type has a β-sheet structure. It has been known that silk becomes enhanced in strength and protein elasticity by the rearrangement of an amorphous state into a β-sheet structure, on the basis of which, various pre-treatment methods for silk proteins have been studied (Nature, 2003, Vol. 424, pp. 1057-1061).

In the present invention, the structure of silk protein was introduced into β-sheet by pre-treating the silk protein with fermented ethanol, and then processes for improving stability and hydrophobicity of the silk protein were added, and therefore, the hydrophobicity of the lactic acid probiotics was increased, and as a result, lactic acid probiotics having enhanced intestinal epithelial cell adhesion and improved stability were manufactured.

In the present invention, in order to coat lactic acid probiotics, silk fibroin was added at a ratio of 1-10% (w/v) relative to the volume of a lactic acid bacteria concentrate, but is not limited thereto.

As used herein, the term "cellulose" refers to the polymer polysaccharide composed of glucose with β-1,4 linkage, and the cellulose is the most abundant polymer on earth. Cellulose is currently used in various fields including papermaking and spinning industries, and is also used for tourniquets, skin substitutes, dietary fibers, and the like (Biowave, 2007, Vol. 9, No. 7, pp. 1-11).

The food additives allowed by the Ministry of Food and Drug Safety of Korea include methylcellulose, carboxymethylcellulose sodium, carboxymethylcellulose calcium, hydroxypropyl methylcellulose, methylcellulose, ethylcellulose, and hydroxypropyl cellulose. Since 1971, hydroxypropyl methylcellulose phthalate (hereinafter, HPMCP) widely used as an enteric coating material has been used as a pharmaceutical additive.

Cellulose has been variously used abroad as an enteric coating agent for tablets, granules, and capsules and as an additive of health functional foods. Especially, HPMCP is a polymer with pH-dependent solubility, which is formed by chemical synthesis using natural pulp as a raw material, and has characteristics in which a carboxyl group substituted on the cellulose ring does not cause disintegration and dissolution in the gastric fluid with a low pH but causes fast disintegration and dissolution in the intestinal fluid with a pH close to neutral.

In the present invention, the lactic acid bacteria cells coated with silk fibroin were coated with cellulose in combination, and thus undergo no disintegration and dissolution in artificial gastric fluid conditions but undergo fast disintegration and dissolution in intestinal fluid conditions with a neutral pH.

In accordance with an aspect of the present invention, there is provided a method for promoting the culture of lactic acid bacteria, the method including culturing lactic acid bacteria in a medium supplemented with silk fibroin.

In the present invention, the culture of lactic acid bacteria is carried out in ordinary lactic acid bacteria culture media and conditions that are known in the conventional art.

Silk fibroin is classified as a protein, which has the highest purity (97%) among the components present in nature, and the silk protein is composed of peptides in which various amino acids as constituent components of the human proteins and binders of the amino acids are present together. In particular, glycine, alanine, and serine, which account for the largest proportion of silk fibroin, account for 70-80% of all the amino acids while tyrosine, valine, aspartate, glutamate, and other amino acids make up the rest. Therefore, these amino acids can be used as important nitrogen source components in the culture of lactic acid bacteria.

According to an embodiment of the present invention, the medium supplemented with silk fibroin of the present invention may contain, on the basis of the volume of the medium, silk fibroin at a concentration of 0.001-5% (w/v), 0.001-4% (w/v), 0.001-3% (w/v), 0.001-2% (w/v), 0.001-1% (w/v), 0.01-5% (w/v), 0.01-4% (w/v), 0.01-3% (w/v), 0.01-2% (w/v), 0.01-1% (w/v), 0.01-0.5% (w/v), 0.01-0.4% (w/v), 0.01-0.3% (w/v), 0.01-0.2% (w/v), 0.1-5% (w/v), 0.1-4% (w/v), 0.1-3% (w/v), 0.1-2% (w/v), 0.1-1% (w/v), 1-5% (w/v), 1-4% (w/v), 1-3% (w/v), 1-2% (w/v), 2-5% (w/v), 2-4% (w/v), 2-3% (w/v), 3-5% (w/v), 3-4% (w/v), or 4-5% (w/v), but is not limited thereto.

As validated in the following examples, it can be seen that the lactic acid bacteria cultured by the method of the present invention showed a promoted growth, leading to shortening of the culture time.

According to an embodiment of the present invention, the medium for culturing lactic acid bacteria of the present invention may further contain water-soluble calcium. As the water-soluble calcium, calcium citrate, calcium hydroxide, calcium chloride, calcium lactate, calcium phosphate dibasic, and calcium phosphate monobasic, which are allowed as food additives, may be used. In addition, the concentration of the water-soluble calcium added may be 0.001-5% (w/v), 0.001-4% (w/v), 0.001-3% (w/v), 0.001-2% (w/v), 0.001-1% (w/v), 0.01-5% (w/v), 0.01-4% (w/v), 0.01-3% (w/v), 0.01-2% (w/v), 0.01-1% (w/v), 0.01-0.5% (w/v), 0.01-0.4% (w/v), or 0.01-0.3% (w/v), preferably 0.01-0.2% (w/v), and most preferably 0.1% (w/v), but is not limited thereto.

According to another embodiment of the present invention, the medium for culturing lactic acid bacteria of the present invention may further contain cellulose. As the cellulose, methylcellulose, carboxymethylcellulose sodium, carboxymethylcellulose calcium, hydroxypropyl methylcellulose, methylcellulose, ethylcellulose, hydroxypropyl cellulose, and hydroxypropyl methylcellulose phthalate (HPMCP), which are allowed as food additives by the Ministry of Food and Drug Safety of Korea, but is not limited thereto.

In accordance with still another aspect of the present invention, there is provided a method for enhancing viability, storage stability, resistance against acid or bile, and intestinal epithelial cell adhesion of lactic acid bacteria, the method including culturing the lactic acid bacteria in a medium containing silk fibroin for culturing lactic acid bacteria.

According to the present invention, when the water-soluble calcium and, additionally, silk fibroin together are added as components of the medium for culturing lactic acid bacteria, the lactic acid produced by the lactic acid bacteria forms salts together with water-soluble calcium and silk fibroin and then aggregate, and as a result, the lactic acid bacteria can be stably coated during culture and concentration thereof.

According to a specific embodiment of the present invention, the lactic acid bacteria coated with silk protein of the present invention can be verified to have effects of enhancing cell hydrophobicity, mucin adhesion, and intestinal epithelial cell adhesion, and the ingestion of the thus manufactured lactic acid probiotics allows the lactic acid bacteria to stably adhere to intestinal epithelial cells, thereby increasing bioactive effects of the lactic acid bacteria.

According to another specific embodiment of the present invention, the lactic acid bacteria co-coated with silk fibroin and cellulose can be verified to have excellent cell hydrophobicity, mucin adhesion, and intestinal epithelial cell adhesion.

According to a still another specific embodiment of the present invention, the lactic acid bacteria composition of the present invention shows excellent stability (viability) in test conditions of resistance against acid and bile to determine intestine tract environment stability and freeze-drying viability and severe test conditions to determine storage stability for existing lactic acid probiotics.

As used herein, the term "resistance against acid" refers to the property of the lactic acid bacteria of the present invention to favorably withstand an acid of pH 7 or lower. Specifically, the resistance against acid used herein refers to the resistance of the lactic acid bacteria against an artificial gastric liquid of pH 1-3, for example, an artificial gastric liquid of pH 2.0 or 2.5, and the viability of the lactic acid bacteria can be measured through comparison of viable cell count between before and after contact with an artificial gastric liquid. According to an embodiment of the present invention, the artificial gastric liquid is prepared by adjusting the pH of an aqueous solution of 1 N hydrochloric acid (HCl) to 2.0 or 2.5, and if necessary, the artificial gastric liquid is prepared by adding pepsin, a secretary enzyme in the stomach, at a predetermined concentration (1-2%), but is not limited thereto.

As used herein, "resistance against bile" refers to the resistance of the lactic acid bacteria of the present invention against bile. Specifically, the resistance against bile used herein refers to the resistance of the lactic acid bacteria against to an artificial intestinal liquid (artificial bile liquid), for example, an artificial intestinal liquid containing 0.1-1% bile acid (oxigall), and the viability of viability of the lactic acid bacteria can be measured through comparison of viable cell count between before and after contact with an artificial intestinal liquid According to an embodiment of the present invention, the artificial intestinal liquid is prepared by adding 0.5% bile acid (oxigall) to a liquid medium, or may be prepared by adding a bile extract, but is not limited thereto.

As used herein, the "freeze-drying" is a lyophilization method that is mainly employed for long-term preservation of lactic acid bacteria, and is usually carried out at −20 to −80° C. In the freeze-drying procedure, the cell activity and viability of the lactic acid bacteria are decreased due to physical and biochemical stresses. The "viability in freeze-drying" is measured through comparison of viable cell count of lactic acid bacteria between before and after freeze-drying. According to an embodiment of the present invention, the viability in freeze-drying is measured by comparing the lactic acid bacteria count (cfu) in a lactic acid bacteria sample, which is obtained after the cells are recovered, frozen at 0 to −45° C., specifically −20 to −45° C., dried in a freeze-drier, disrupted, powdered, and then again cultured in a medium, with the lactic acid bacteria count (cfu) in the sample before the freeze-drying, but is not limited thereto.

As used herein, the term "severe test conditions" refers to conditions for measuring the resistance of lactic acid bacteria against external conditions, and mainly means resistance against high temperature and high humidity. According to an embodiment of the present invention, the severe test conditions may be 40° C. and 70-75% humidity, but is not limited thereto.

The intestinal epithelial cell adhesion of the lactic acid bacteria is known to be affected according to the viability of the lactic acid bacteria, host cell adhesion thereof, and correlation thereof with other bacteria, and greatly affected by, specifically, the cell surface feature of lactic acid bacteria cells. The cell surface feature affecting the adhesion ability of the lactic acid bacteria cells is greatly associated with the electrostatic balance, Van der Waals force, and hydrophobicity of the cell surface. Especially, the hydrophobicity of the cell surface is an indicator that is correlated with adhesion between bacteria cells and intestinal epithelial cells, and is used as an important indicator to identify the adhesion ability of lactic acid bacteria strains including *Lactobacillus, Bifidobacterium*, and the like (Letters in Applied Microbiology, 1998, Vol. 27, pp. 307-310).

In the present invention, the hydrophobicity of cell surface is attained by coating lactic acid bacteria cells with silk fibroin. Especially, the structure of the silk fibroin is induced into a β-sheet structure by pre-treatment of the silk fibroin, thereby increasing the hydrophobicity of the surface of the lactic acid bacteria cells coated with the silk fibroin, leading to an enhancement of adhesion ability of the lactic acid bacteria cells to intestinal mucosal cells. Since the 1-sheet structure is more resistant against heat than the alpha-helix structure, the β-sheet structure can improve stability and exhibit hydrophobicity when used as a coating agent.

The lactic acid bacteria used in the present invention is not particularly limited to the kind thereof, and for example, the lactic acid bacteria may be selected from the group consisting of the genera *Lactobacillus, Lactococcus, Enterococcus, Streptococcus*, and *Bifidobacterium*.

According to another embodiment of the present invention, the lactic acid bacteria may be specifically selected from the group consisting of *Lactobacillus acidophilus, Lactobacillus plantarum, Lactobacillus delbrueckii* ssp. *bulgaricus, Lactococcus lactis, Enterococcus faecium, Enterococcus faecalis, Streptococcus thermophilus, Bifidobacterium bifidum*, and *Bifidobacterium lactis*.

According to still another embodiment of the present invention, the lactic acid bacteria may be, most specifically, selected from the group consisting of *Lactobacillus acidophilus* CKDB007 (Accession No.: KCTC13117BP), *Enterococcus faecium* CKDB003 (Accession No.: KCTC13115BP), *Streptococcus thermophilus* CKDB021 (Accession No.: KCTC13118BP), *Bifidobacterium bifidum* CKDB001 (Accession No.: KCTC13114BP), and *Bifidobacterium lactis* CKDB005 (Accession No.: KCTC13116BP).

According to still another embodiment of the present invention, the composition characterized by the lactic acid bacteria, of the present invention, may be selected from the group consisting of a food composition, a probiotic composition, and a feed composition.

The composition of the present invention, when prepared into a food composition, may contain an ingredient ordinarily added in the manufacture of foods as well as the lactic acid bacteria as an active ingredient. The additional ingredient includes, for example, a protein, a carbohydrate, a fat, a nutrient, a seasoning, and a flavoring agent. Examples of the carbohydrate may include typical sugars, such as monosaccharides (e.g., glucose, fructose, etc.), disaccharides (e.g., maltose, sucrose, oligosaccharides, etc.), and polysaccharides (e.g., dextrin, cyclodextrin, etc.), and sugar alcohols, such as xylitol, sorbitol, and erythritol. Examples of the flavoring agent may include natural flavoring agents (thaumatin, and *stevia* extracts (e.g., rebaudioside A, glycyrrhizin, etc.)) and synthetic flavoring agents (saccharin, aspartame, etc.).

For example, the food composition of the present invention, when manufactured into a drink, may further contain citric acid, liquefied fructose, sugar, glucose, acetic acid, malic acid, fruit juice, a jujube extract, or a licorice extract, in addition to the strain as an active ingredient of the present invention.

The food composition of the present invention includes all the processed types of natural materials, such as foods, functional foods, nutritional supplements, health foods, and food additives. The above types of food composition may be manufactured in various forms according to the conventional methods known in the art.

For example, as for health foods, the lactic acid bacteria per se may be manufactured in the forms of a tea, a juice, and a drink so as to be ingested, or the lactic acid bacteria may be granulized, encapsulated, or powdered so as to be ingested. As for foods, beverages (including alcoholic beverages), fruits and processed foods thereof (e.g., canned fruit, bottled food, jam, marmalade, etc.), fishes, meats and processed products thereof (e.g., ham, sausage, corned beef, etc.), breads, noodles (e.g., udong, buckwheat noodles, ramen, spaghetti, macaroni, etc.), fruit juices, a variety of drinks, cookies, syrups, dairy products (e.g., butter, cheese, etc.), edible vegetable oils, margarine, vegetable proteins, retort foods, frozen foods, various seasonings (e.g., soybean paste, soybean sauce, sauces, etc.), and the like may be manufactured by addition of the lactic acid bacteria of the present invention. In addition, in order to use the lactic acid bacteria of the present invention in the form of a food additive, the lactic acid bacteria may be manufactured in the form of a powder or concentrate.

In cases where the composition of the present invention is prepared into a pharmaceutical composition, the pharmaceutical composition of the present invention contains a pharmaceutically acceptable carrier. The pharmaceutically acceptable carrier contained in the pharmaceutical composition of the present invention is ordinarily used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oils. The pharmaceutical composition of the present invention may further contain, in addition to the above ingredients, a lubricant, a wetting agent, a sweetening agent, a flavoring agent, an emulsifier, a suspending agent, a preservative, and the like.

The pharmaceutical composition of the present invention may be administered orally or parenterally, and preferably, the oral administration manner is employed. The pharmaceutical composition of the present invention may be formulated in various forms of oral or parenteral administration, but is not limited thereto.

The formulations for oral administration include, for example, a tablet, a pill, a soft/hard capsule, a liquid, a suspension, an emulsifier, syrup, granules, an elixir, and the like. These formulations may employ, in addition to the active ingredient, at least one diluent or excipient, such as a filler, an extender, a wetting agent, a disintegrant, a lubricant, a binder, and a surfactant, which are usually used in the art. Agar, starch, alginic acid or sodium salt thereof, and anhydrous calcium monohydrogen phosphate may be used as a disintegrant; silica, talc, stearic acid or magnesium salt or calcium salt thereof, and polyethylene glycol may be used as a lubricant; and magnesium aluminum silicate, starch paste, gelatin, tragacanth, methylcellulose, carboxymethylcellulose sodium, polyvinylpyrrolidone, and low-substituted hydroxypropyl cellulose may be used as a binder. Besides, lactose, dextrose, sucrose, mannitol, sorbitol, cellulose, or glycine may be used as a diluent, and in some cases, an azeotropic mixture, an absorbent, a colorant, a flavoring agent, a sweetening agent, and the like, which are generally known in the art, may be used together.

The composition may be sterilized, or may contain an adjuvant, such as a preservative, a stabilizer, a wettable powder, or an emulsification accelerator, a salt for controlling osmotic pressure, or a buffer, and other therapeutically beneficial substances, and may be formulated according to a conventional method, such as mixing, granulation, or coating.

A suitable dose of the pharmaceutical composition of the present invention may be variously prescribed according to various factors, such as the method of formulation, the manner of administration, the patient's age, body weight, gender, morbidity, and diet, the time of administration, the route of administration, the excretion rate, and the response sensitivity.

The pharmaceutical composition of the present invention is formulated using a pharmaceutically acceptable carrier and/or excipient according to a method that is easily conducted by a person having ordinary skills in the art to which the present invention pertains, so that the composition may be prepared in a unit dosage form or may be contained in a multi-dose container. Here, the formulation may be in the form of a solution in an oily or aqueous medium, a suspension, a syrup, an emulsion, an extract, a pulvis, a powder, a granule, a tablet, or a capsule, and may contain a dispersant or a stabilizer.

The lactic acid bacteria coated with silk fibroin and the composition containing the lactic acid bacteria, a method for promoting the culture of lactic acid bacteria by adding silk fibroin to a medium for culturing lactic acid bacteria, a method for manufacturing lactic acid bacteria coated with silk fibroin, and a method for enhancing viability, storage stability, resistance against acid or bile, and intestinal epithelial adhesion of lactic acid bacteria may be cross-applied with each other. The lactic acid composition manufactured by the above techniques may be applied as a food composition, a health functional food, and a pharmaceutical composition. The description of overlapping contents therebetween will be omitted to avoid complexity of the specification.

Advantageous Effects

Features and advantages of the present invention are summarized as follows.

(i) The present invention provides a composition containing lactic acid bacteria coated with silk fibroin or lactic acid bacteria coated with silk fibroin and cellulose.

The present invention also provides a method for promoting the culture of lactic acid bacteria, the method including culturing lactic acid bacteria in a medium supplemented with silk fibroin.

The present invention also provides a method for enhancing viability, storage stability, resistance against acid or bile, and intestinal epithelial cell adhesion of lactic acid bacteria.

(ii) It was verified in the present invention that the coating of lactic acid bacteria cells with silk fibroin manufactured through various treatment methods induced effects of improving viability and storage stability of the lactic acid bacteria cells, exhibiting excellent resistance against acid or bile of the lactic acid bacteria, and enhancing intestinal epithelial cell adhesion of the lactic acid bacteria.

DETAILED DESCRIPTION

Hereinafter, the present invention will be described in more detail with reference to examples. These examples are only for illustrating the present invention more specifically, and it will be apparent to those skilled in the art that the scope of the present invention is not limited by these examples.

Throughout the present specification, the term "%" used to express the concentration of a specific material, unless otherwise particularly stated, refers to (wt/wt) % for solid/solid, (wt/vol) % for solid/liquid, and (vol/vol) % for liquid/liquid.

EXAMPLES

Figure 1:
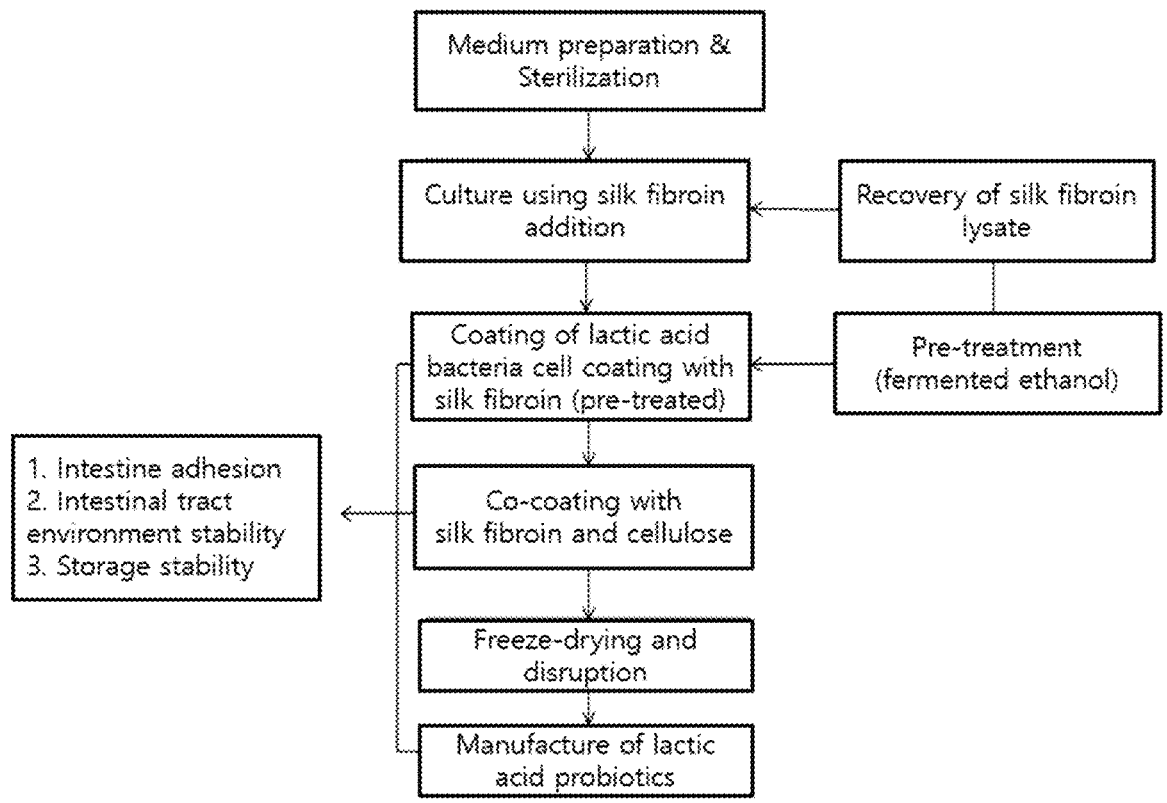
FIG. 1 is a diagram showing a process for manufacturing lactic acid probiotics by using silk fibroin.

The present inventors conducted the following tests to investigate the effects of the addition and coating of silk fibroin of the present invention on lactic acid bacteria. FIG. 1 is a process diagram showing the order and contents of the tests conducted by the present inventors.

Example 1: Isolation and Purification of Silk Fibroin Component of the Present Invention Silk is a giant protein that can be obtained from nature, and silk fibroin is composed of 18 types of amino acids among 20 types of amino acids constituting human proteins. Liquid silk, which is bio-synthesized from silk glands of silkworms consisting of 18 types of natural amino acids, has a fiber arrangement with a high degree of crystallization through silkworm vomiting and consists of two components, fibroin (approximately 75%) and sericin (approximately 25%).

Methods for obtaining silk fibroin may be largely divided into (i) acid hydrolysis and (ii) protein hydrolysis by a calcium chloride solution and an enzyme. The silk fibroin used in the coating of lactic acid bacteria cell in the present invention was obtained by a refining process of separating and removing the sericin component from cocoons obtained by growing silkworms (*Bombyx hori*).

Example 1-1: Acid Hydrolysis

In order to isolate silk fibroin, purified water was warmed (95° C.), and then sodium oleate and $Na_2CO_3$ were added and completely dissolved. Thereafter, cocoons were added thereto, followed by boiling for about 40 minutes and then dehydration, thereby refining the cocoons. Specifically, for the refining, cocoons, sodium oleate, and $Na_2CO_3$ were added to the purified water at concentrations of 1.84% (w/v), 0.0092% (w/v), and 0.0055% (w/v), respectively. 2N HCl usually used in acid hydrolysis was added thereto, followed by acid hydrolysis in a temperature condition of 110° C. for 2 hours, and then the solution obtained after the hydrolysis was filtered, and neutralized with an aqueous solution of NaOH. The salts formed during the neutralization process were removed by dialysis the tubing cellulose membrane, thereby manufacturing purified acid-hydrolyzed silk fibroin. It is known that the average molecular weight of the peptides obtained through acid hydrolysis is generally about 200-10,000, and thus silk fibroin, a relatively small peptide, can be obtained.

Example 1-2: Enzymatic Hydrolysis

In order to isolate silk fibroin, the cocoons were refined by the same method as in Example 1-1. Then, Alcalase, Delvorase, Flavourzyme, or Protamax (Vision Biochem Co., Ltd.), which is known as the protease produced by *Bacillus licheniformis, Bacillus stearothermophilus*, or *Aspergillus niger*, and Papain T100 (Vision Biochem Co., Ltd.) recovered from *papaya* were added at a concentration of 5%, followed by the treatment of the cocoons in a temperature condition of 60-80° C. for 6-10 hours. The silk fibroin solution obtained from hydrolysis was exposed to a high-temperature condition of 95° C. for 2 hours to inactivate the protease before use in the lactic acid bacteria coating process. The silk fibroin manufactured by such enzymatic hydrolysis is known to be high in solubility and body absorption rate.

In order to investigate the effects of the silk fibroin of the present invention on the promotion of culturing lactic acid bacteria cells and the cell coating effects, the silk fibroin proteins manufactured by the above methods (acid hydrolysis and enzymatic hydrolysis) were respectively recovered, and then applied to cell culture and cell coating for *Enterococcus faecium* CKDB003 (Accession No.: KCTC13115BP), *Lactobacillus acidophilus* CKDB007 (Accession No.: KCTC13117BP), *Streptococcus thermophilus* CKDB021 (Accession No.: KCTC13118BP), *Bifidobacterium lactis* CKDB005 (Accession No.: KCTC13116BP), and *Bifidobacterium bifidum* CKDB001 (Accession No.: KCTC13114BP)

Example 2: Use of Silk Fibroin Component of Present Invention

The silk protein, which contains sericin and fibroin as main components, recovered from the cocoons, is composed of 75% fibroin protein, 25% sericin protein, and about 3% minerals and carbohydrates.

Silk fibroin is classified as a protein, which has the highest purity (97%) among the components present in nature, and the silk protein is composed of peptides in which various amino acids as constituent components of the human proteins and binders of the amino acids are present together.

In particular, glycine, alanine, and serine, which account for the largest proportion of silk fibroin, account for 70-80% of all the amino acids, and the above amino acid components constituting silk fibroin are known to be amino acid components constituting collagen. Therefore, this silk fibroin is strong like collagen, and the constituent amino acids may be used as important nitrogen source components in the culture of lactic acid bacteria.

Example 2-1: Use of Silk Fibroin as Component for Culturing Lactic Acid Bacteria In order to investigate the effects of silk fibroin of the present invention on the culture characteristics of lactic acid bacteria when the silk fibroin was used as a component for culturing lactic acid bacteria, optimized medium and culture conditions known for respective bacteria species were used. The lactic acid bacteria cultured in the optimal culture composition were used as a control group, and the lactic acid bacteria cultured with addition of silk fibroin in the same culture conditions were used as a test group. The carbon source consumption rate (%) and viable cell count over time were compared between the control group and the test group.

Figure 2A:
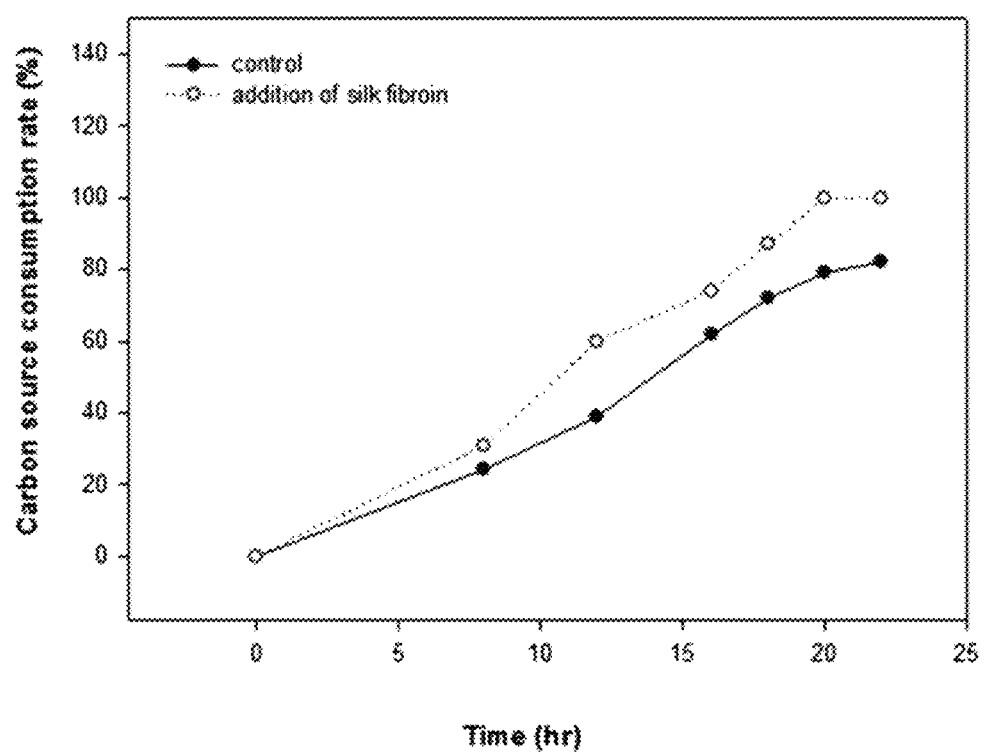
FIGS. 2A and 2B show comparisons of the carbon source consumption pattern and culture characteristics when silk fibroin was used for a medium for lactic acid bacteria.

The results are shown in FIGS. 2a and 7b.

Figure 2B:
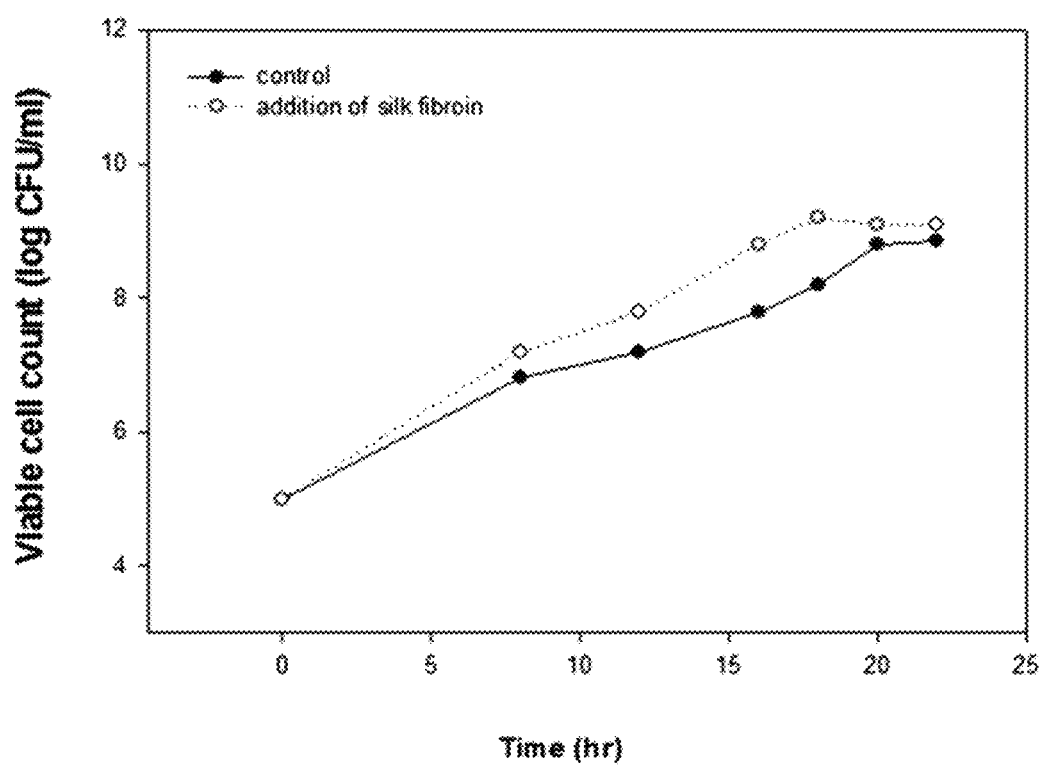

As shown in FIGS. 2a and 2b, the lactic acid bacteria cultured by addition of silk fibroin of the present invention showed a very fast sugar consumption rate at the early stage of culture compared with the lactic acid bacteria cultured without addition of fibroin (FIG. 2a). It was also verified that culturing of the lactic acid bacteria through addition of silk fibroin shortened the time point showing optimal culture characteristics at the latter stage of culture (FIG. 2b).

It can be therefore seen from the above results that the silk fibroin component of the present invention acts as an important growth factor in the growth of lactic acid bacteria, thereby promoting the culture of lactic acid bacteria and shortening the time of culture. FIG. 1 shows the culture characteristics results of the bacterial species *Bifidobacterium lactis* CKDB005 (Accession No.: KCTC13116BP). The culture characteristics results of the other bacterial species are not shown, but were verified to show similar effects to the bacterial species *Bifidobacterium lactis*.

Example 2-2: Use of Water-Soluble Calcium and Silk Fibroin as Components for Culturing Lactic Acid Bacteria The present inventors verified that when water-soluble calcium and silk fibroin are provided together as medium components for culturing lactic acid bacteria, the culture characteristics of the lactic acid bacteria can be improved, and the lactic acid produced by the lactic acid bacteria forms salts together with water-soluble calcium and silk fibroin and then aggregate, and as a result, the lactic acid bacteria can be stably coated during culture and concentration thereof. Furthermore, in order to establish the optimal conditions for coating the surface of the lactic acid bacteria cells with silk fibroin and investigate the coating effect of the lactic add bacteria with silk fibroin on the stability of the lactic acid bacteria, the following test was conducted.

First, the silk fibroin used in the culture employed the dried powder prepared through the method in Example 1, and the concentration of silk fibroin added was 0-3% (w/v) relative to the volume of the culture. The water-soluble calcium additionally added employed calcium citrate, calcium hydroxide, calcium chloride, calcium lactate, calcium phosphate dibasic, and calcium phosphate monobasic, which are allowed as food additives. The lactic acid bacteria were cultured while the addition concentration thereof was 0, 0.1, and 0.5% (w/v) each, thereby manufacturing lactic acid probiotics coated with silk fibroin.

Then, comparison was conducted for the viability in freeze-drying and the viability in severe conditions (40° C. and 70-75% humidity) of the manufactured lactic acid probiotics. Cell recovery and freeze-drying were conducted by ordinary methods (cell recovery through centrifugation, quick freezing in a freezer at −40° C., and then freeze-drying in freeze-drying conditions between 0 to −45° C.), and the viability in freeze-drying was determined as a percentage of the viable cell count after freeze-drying divided by the viable cell count before freeze-drying.

Meanwhile, the viability in severe conditions was determined by identifying the viable cell count after the lactic acid probiotics were stored for 4 weeks in severe conditions (40° C. and 70-75% humidity).

TABLE 1

Viability in freeze-drying (%)

| Strain | Calcium concentration, % (w/v) | | |
|---|---|---|---|
| | 0 | 0.1 | 1 |
| E.faecium CKDB003 | 64 | 71 | 68 |
| S.thermophilus CKDB021 | 50 | 55 | 51 |
| B.lactis CKDB005 | 26 | 31 | 28 |
| B.bifidum CKDB001 | 20 | 24 | 20 |
| L.acidophilus CKDB007 | 22 | 30 | 24 |

TABLE 2

Stability in severe conditions (temperature of 40° C. and 70% humidity)

| Strain | CFU/g Calcium concentration, % (w/v) | | | Viability (%) Calcium concentration, % (w/v) | | |
|---|---|---|---|---|---|---|
| | 0 | 0.1 | 0.5 | 0 | 0.1 | 0.5 |
| E. faecium CKDB003 | 1.75E+11 | 2.03E+11 | 1.94E+11 | 76 | 81 | 76 |
| S. thermophilus CKDB021 | 8.82E+10 | 1.20E+11 | 1.09E+11 | 42 | 45 | 43 |
| B. lactis CKDB005 | 3.00E+10 | 5.25E+10 | 5.04E+10 | 27 | 31 | 28 |
| B. bifidum CKDB001 | 9.00E+09 | 1.32E+10 | 1.21E+10 | 20 | 24 | 20 |
| L. acidophilus CKDB007 | 1.65E+10 | 3.75E+10 | 3.04E+10 | 18 | 25 | 22 |

As shown in Tables 1 and 2, it was verified that the addition of the silk fibroin of the present invention together with water-soluble calcium leaded to excellent viability in freeze-drying and viability in severe conditions, and especially, showed most excellent viability of lactic acid bacteria at a calcium concentration of 0.1% (w/v).

Example 2-3: Use of Silk Fibroin in Culture and Coating

After the verification of the improvement in culture characteristics and stability of lactic acid bacteria when silk fibroin and water-soluble calcium were used in a medium for culturing lactic acid bacteria as confirmed in Examples 2-1 and 2-2, lactic acid probiotics were manufactured as below.

For preparation of a control group (uncoated), a separate coating process is not conducted after cell culture and concentration using an optimized culture medium. For a test group, silk fibroin and water-soluble calcium were added together as medium components in the culture of lactic acid bacteria, and then the lactic acid bacteria were cultured and concentrated, and then coated with silk fibroin.

The coating of lactic acid bacteria was conducted by employing an ordinary method (Example 2-2), and the lactic acid probiotics were disrupted using a disruptor, and then applied to respective test examples of Example 4.

Example 3: Manufacture of Lactic Acid Probiotics Coated with Fermented Ethanol-Pre-Treated Silk Fibroin In order to establish optimal silk fibroin for being coated on lactic acid bacteria cells and investigate the effect on the coating quality of lactic acid bacteria according to the conditions of the applied silk fibroin, the silk fibroin was pre-treated with fermented ethanol. Specifically, the silk fibroin manufactured by enzymatic hydrolysis in Example 1-2 of the present invention was mixed with fermented ethanol at a proportion of 30%, and then the mixture was homogenized in the aseptic condition and room-temperature condition (25° C.), and allowed to stand for 18-24 hours.

In Example 3, the lactic acid bacteria were cultured and coated by the same method in Example 2-2 except that the silk fibroin pre-treated with fermented ethanol as above was used instead of silk fibroin undergoing no pre-treatment.

Example 4: Manufacture of Lactic Acid Probiotics Co-Coated with Silk Fibroin and Cellulose In order to improve characteristics of lactic acid probiotics coated with the silk fibroin and the resistance thereof against an intestine tract environment, lactic acid bacteria co-coated with the silk fibroin of the present invention and cellulose used as a conventional enteric coating material were manufactured.

Specifically, the dried powder manufactured by the method as in Example 1 was used as the silk fibroin for coating lactic acid probiotics, and the silk fibroin treated with fermented ethanol was added at a ratio of 1-10% (w/v) relative to the volume of the lactic acid bacteria concentrate. As for the cellulose, methylcellulose, carboxymethylcellulose sodium, carboxymethylcellulose calcium, hydroxypropyl methylcellulose, methylcellulose, ethylcellulose, hydroxypropyl cellulose, and hydroxypropyl methylcellulose phthalate (HPMCP), which are allowed as food additives by the Ministry of Food and Drug Safety of Korea, were applied as a coating agent. As described in the following test examples, the results verified that when lactic acid probiotics were coated by adding HPMCP (Any Coast (medical brand name), Samsung Fine Chemicals) and carboxymethyl cellulose sodium (Samsung Fine Chemicals) at a proportion of 1-10% relative to the volume of the lactic acid concentrate, the viability in freeze-drying and the viability in severe conditions (40° C. and 70% humidity) of the lactic acid bacteria were improved.

Test Examples

The present inventors conducted the following tests as below in order to investigate the characteristics of lactic acid probiotics depending on coating with the silk fibroins manufactured in Examples 2 to 4 and coating method therefor.

The control and test groups used in the following test examples are shown in Table 3.

TABLE 3

| Classification | Lactic acid coating method |
|---|---|
| Control group | Example 2-3: Non-addition (uncoated control group) |
| Test group 1: | Example 2-3: Coated with silk fibroin |
| Test group 2: | Example 3: Coated with fermented ethanol-pre-treated silk fibroin |
| Test group 3: | Example 4: Co-coated with fermented ethanol-pre-treated silk fibroin and cellulose |

Test Example 1: Investigation of Coating Efficiency of Lactic Acid Probiotics Depending on Coating Conditions of Silk Fibroin The samples of the control group (Example 2-3, lactic acid probiotics of uncoated control group), test group 1 (Example 2-3, lactic acid probiotics coated with silk fibroin), test group 2 (Example 3, lactic acid probiotics coated with fermented ethanol-pre-treated silk fibroin), and test group 3 (Example 4, lactic acid probiotics coated with fermented ethanol-pre-treated silk fibroin and cellulose) as shown in Table 3 were immobilized on respective metal plates by using carbon tapes, platinum-coated by a plasma sputter, and then observed at an accelerated voltage of 10 kV using EBSD/FE-SEM (scanning electron detector).

Figure 3:
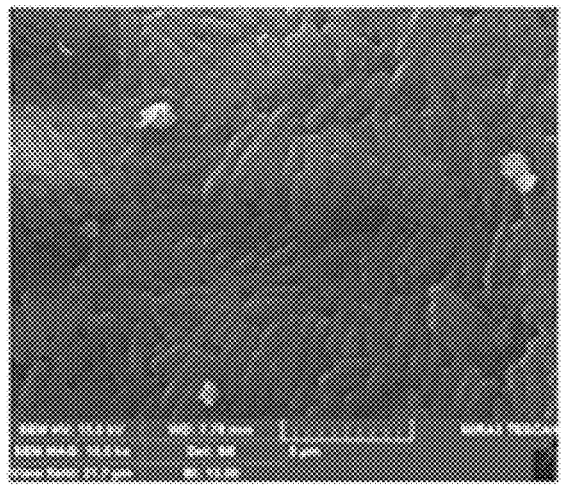
FIG. 3 provides images obtained by observing the morphology of lactic acid probiotics manufactured using silk fibroin and cellulose through EBSD/FE-SEM (scanning electron microscope detector).
Figure 3:
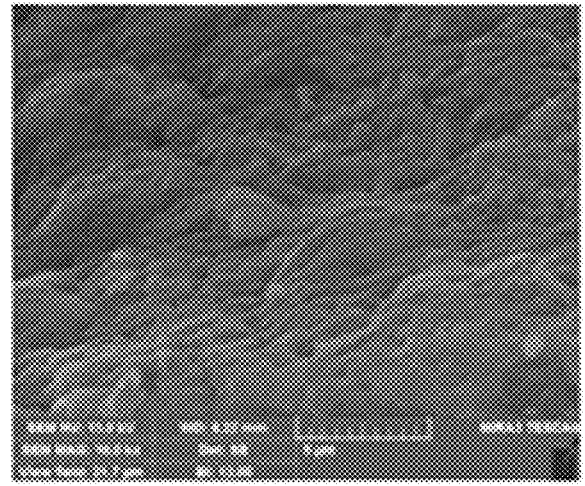
Figure 3:
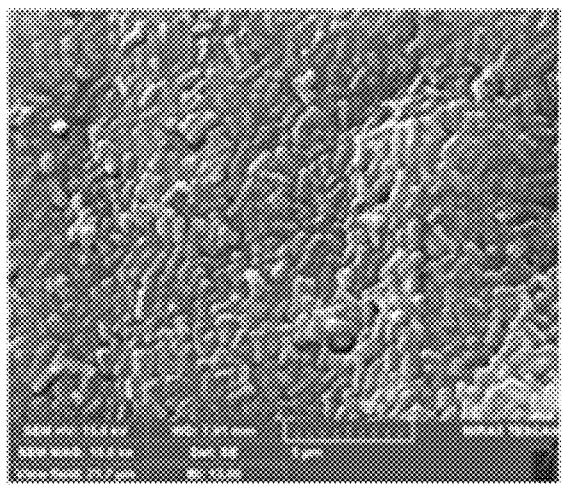
Figure 3:
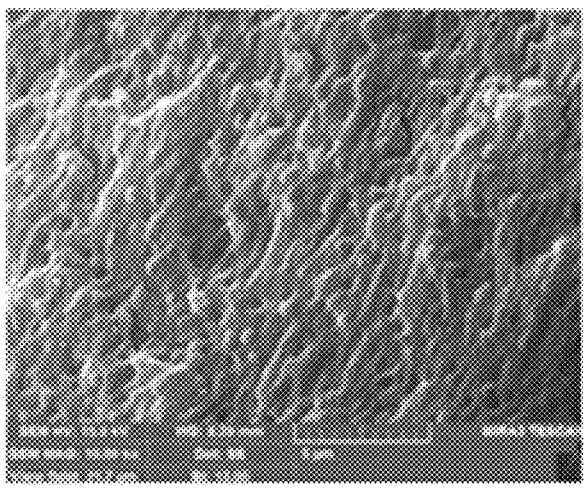

The results are shown FIG. 3.

As shown in FIG. 3, it was observed that the probiotics manufactured by coating lactic acid bacteria cells with only silk fibroin (test group 1) had favorable coating morphology compared with the control group (uncoated), but had partially uncoated cells. It was also verified that the cells were overall uniformly enclosed in the silk lactic acid probiotics coated with silk fibroin manufactured by fermented ethanol pretreatment (test group 2), and the cells were coated more uniformly in the lactic acid probiotics co-coated with fermented ethanol-treated silk fibroin and cellulose (test group 3) than the lactic acid probiotic coated with only fermented ethanol-treated silk fibroin (test group 2). Therefore, it can be seen that the coating quality was most excellent in the probiotics of test group 1 rather than the control group, test group 2 rather than test group 1, and test group 3 rather than test group 2.

In the present example, the treatment with the fermented ethanol is for inducing silk fibroin to have a β-sheet structure through regeneration and treatment and preventing enzymatic hydrolysis of lactic acid bacteria and silk fibroin in a coating process through inactivation of the enzyme used in the enzymatic hydrolysis.

Test Example 2: Surface Hydrophobicity of Lactic Acid Bacteria Cells Depending on Coating Method of Silk Fibroin The cell surface hydrophobicity is an indicator to indirectly provide the intestinal adhesion ability of lactic acid bacteria in vitro, and is used as one of primary selection methods to identify the adhesion ability of lactic acid bacteria including *Lactobacillus* and *Bifidobacterium*. In order to investigate the hydrophobicity of the lactic acid probiotics coated with silk fibroin, the following test was conducted as below.

Specifically, the uncoated lactic acid probiotics (control group) and lactic acid probiotics manufactured according to respective coating conditions (test groups) were washed two times with 1× phosphate buffered saline (PBS, pH 7.2) and then suspended in 1×PBS to $OD_{600}=0.5$ of cells. The lactic acid bacteria samples prepared after the suspension were mixed with added toluene, followed by treatment in a water bath at 37° C. for 20 minutes, and then the toluene was removed, and the $OD_{600}$ value of the aqueous solution layer was measured. The hydrophobicity of the lactic acid probiotics was calculated by the following equation.

$$\frac{(\text{Early lactic acid probiotic suspension } OD_{600}) - (\text{lactic acid probiotic supernatant } OD_{600})}{(\text{Early lactic acid probiotic suspension } OD_{600})} \times 100 = \text{hydrophobicity}(\%)$$

The results are shown in Table 4.

TABLE 4

| | Cell surface hydrophobicity (%) | | | |
|---|---|---|---|---|
| Strain | Uncoated | Silk fibroin coating (acid hydrolysis) | Silk fibroin coating (enzymatic hydrolysis) | Silk fibroin coating (addition of pre-treatment with fermented ethanol after enzymatic hydrolysis) |
| E.faecium CKDB003 | 49 | 52 | 64 | 72 |
| S.thermophilus CKDB021 | 57 | 57 | 61 | 67 |
| B.lactis CKDB005 | 65 | 68 | 70 | 78 |
| B.bifidum CKDB001 | 35 | 33 | 38 | 43 |
| L.acidophilus CKDB007 | 50 | 48 | 50 | 52 |

As shown in Table 4, it was verified that the coating of lactic acid bacteria with silk fibroin showed improved hydrophobicity of cells compared with the uncoated control group. It was also verified that the hydrophobicity of the lactic acid probiotics was overall high in the lactic acid bacteria coated with the silk fibroin manufactured by enzymatic hydrolysis compared with the silk fibroin manufactured by acid hydrolysis, and especially, the hydrophobicity of the cells was further improved when the lactic acid bacteria cells were coated with silk fibroin pre-treated with fermented ethanol.

Test Example 3: Surface Zeta-Potential of Lactic Acid Bacteria Cells Depending on Coating Method of Silk Fibroin The zeta-potential also called electrokinetic potential refers to a potential difference across a fluidized bed of an electric double layer, generated due to electrodynamic phenomena. The potential of the membrane surface cannot be directly measured, but instead, the zeta potential can be measured through tests to determine electrochemical properties of the surface (Chemistry of the solid-water interface, John Wiley & Sons, Inc, 1992). The zeta potential is an important parameter to determine the stability or aggregation of dispersed particles, and may have an important meaning to determine the effects of products in the body when the lactic acid probiotics were ingested. Regarding microparticles or colloids, as the absolute value of the zeta potential increases, the repulsion between particles is stronger, leading to increased particle stability, but as the zeta potential approaches zero, the particles aggregate more easily. In the present invention, the average value of analysis results obtained from five times of measurements using a zeta potential analyzer using phase analysis light scattering (PALS) was calculated and used.

Specifically, the lactic acid probiotics uncoated (control group), coated with silk fibroin (test group 1), coated with fermented ethanol-pre-treated silk fibroin (test group 2), and coated with silk fibroin and cellulose (test group 3) were manufactured in an aqueous solution phase, which is a test condition artificially simulating an intestinal tract environment, and then the zeta potential values were identified.

Figure 4:
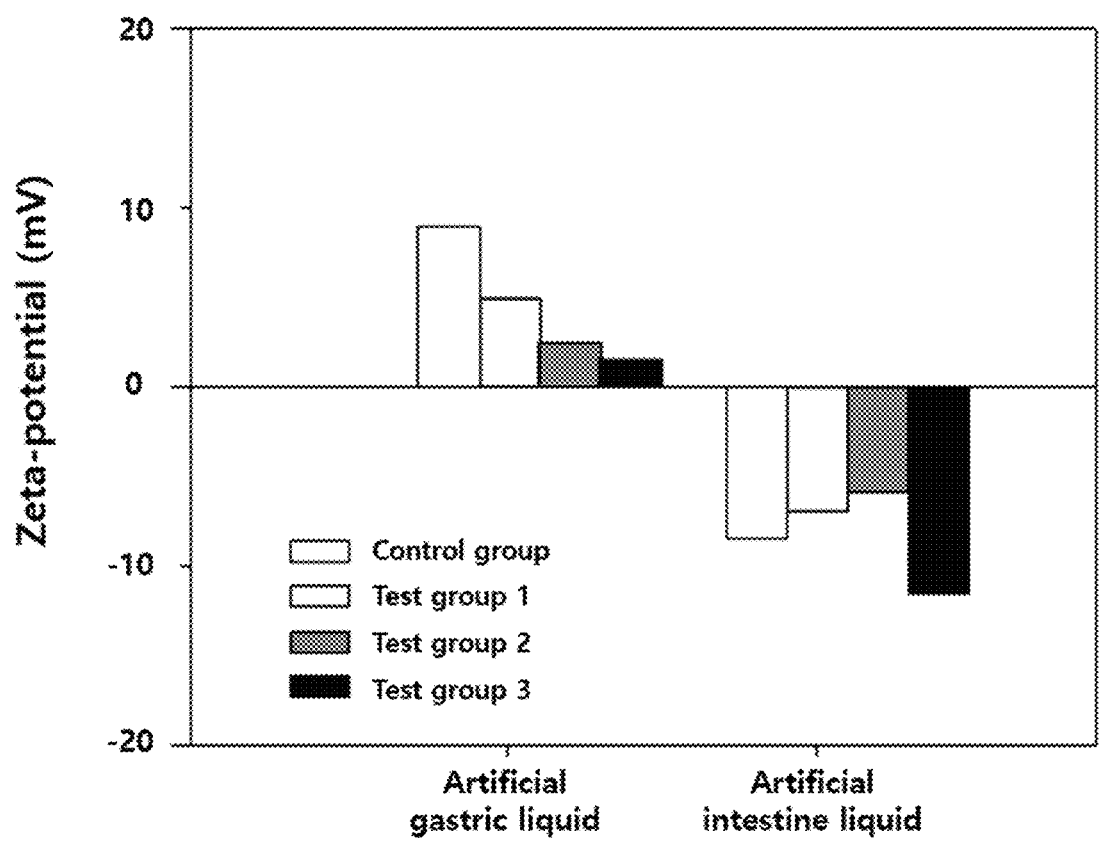
FIG. 4 shows comparisons of zeta-potential of lactic acid probiotics coated with silk fibroin according to artificial gastric liquid and artificial intestinal liquid conditions.

The results are shown FIG. 4.

As shown in FIG. 4, it was verified that in artificial gastric liquid conditions (an aqueous solution in conditions of 2.0 g of sodium chloride, 24.0 ml/L diluted hydrochloric acid, and pH 1.2), the lactic acid probiotics coated with silk fibroin or fermented ethanol-pre-treated silk fibroin (test groups 1 and 2) showed small zeta potential values compared with the control group, and the lactic acid probiotics co-coated with pretreated silk fibroin and cellulose showed a smaller zeta potential value (test group 3).

In addition, the zeta potential values of all the test groups showed negative values in artificial intestine liquid conditions (an aqueous solution in conditions of 0.3% bile acid and pH 7.0). It was verified that the zeta potential absolute value was decreased by stages in the lactic acid probiotics coated with silk fibroin or fermented ethanol-pre-treated silk fibroin (test groups 1 and 2) compared with the control group, but the zeta potential absolute value was rather increased in the lactic acid probiotics co-coated with pre-treated silk fibroin and cellulose. These results indirectly indicate that in artificial intestine liquid conditions, the hydrophobicity of the lactic acid bacteria cells coated with silk fibroin was increased and the hydrophobicity of the lactic acid bacteria cells co-coated with silk fibroin and cellulose was decreased.

Therefore, it was experimentally verified through the measurement of zeta potential values that the lactic acid probiotics co-coated with silk fibroin and cellulose of the present invention showed high viability of lactic acid bacteria cells through strong aggregation in artificial gastric liquid conditions, and when the probiotics reached the small and large intestines, the cellulose layer was eluted to lower the zeta potential absolute value, and thus the silk fibroin-coated lactic acid bacteria showed increased intestine adhesion, thereby increasing the likelihood of stable survival in the intestinal tract environment.

Test Example 4: Mucin-Binding Ability of Lactic Acid Bacteria Cells Depending on Coating Method of Silk Fibroin The adhesion ability of microorganisms is associated with electrostatic balances, Van der Waals bonds, and hydrophobicity of cell walls. The hydrophobicity is known to be an important factor for bacteria cells to adhere to mucosal or epithelial cells (Environ Microbiol, 2000, Vol. 66(6), pp. 2548-2554; and International Dairy Journal, 2005, Vol. 15, pp. 1289-1297).

Especially, intestinal epithelial cells produce mucin, a gel-like substance, to form a membrane protecting barriers. Since mucin, an intestinal mucosa component, enables hydrophobic binding with lactic acid bacteria, lactic acid bacteria having high hydrophobic characteristics are also expected to have excellent intestinal adhesion. In the present invention, the binding ability of lactic acid bacteria cells to mucin was investigated by evaluating the adhesion ability of the respective lactic acid bacteria to mucin, an intestinal mucosal component. The mucin adhesion ability was tested by applying Munoz-Provencio (Gastroenterology. 1998, Vol. 115, pp 874-882).

First, porcine stomach mucin, type II (sigma) was dispensed 200 µL each in the Maxisorb plate known as ELISA plate, and allowed to adhere thereto at 4° C. for 24 hours. Then, as shown in Table 3, the lactic acid probiotics coated with silk fibroin and the uncoated probiotics were suspended to reach $OD_{600}$=0.5, and then dispensed 200 µL each in the Maxisorb plate coated with mucin, followed by incubation at 4° C. overnight (12 hours or longer). After the incubation, the lactic acid bacteria cells not adhering to mucin were removed by washing five times using a PBS buffer, and stained with crystal violet, and then the absorbance was measured at $OD_{620}$.

Figure 5:
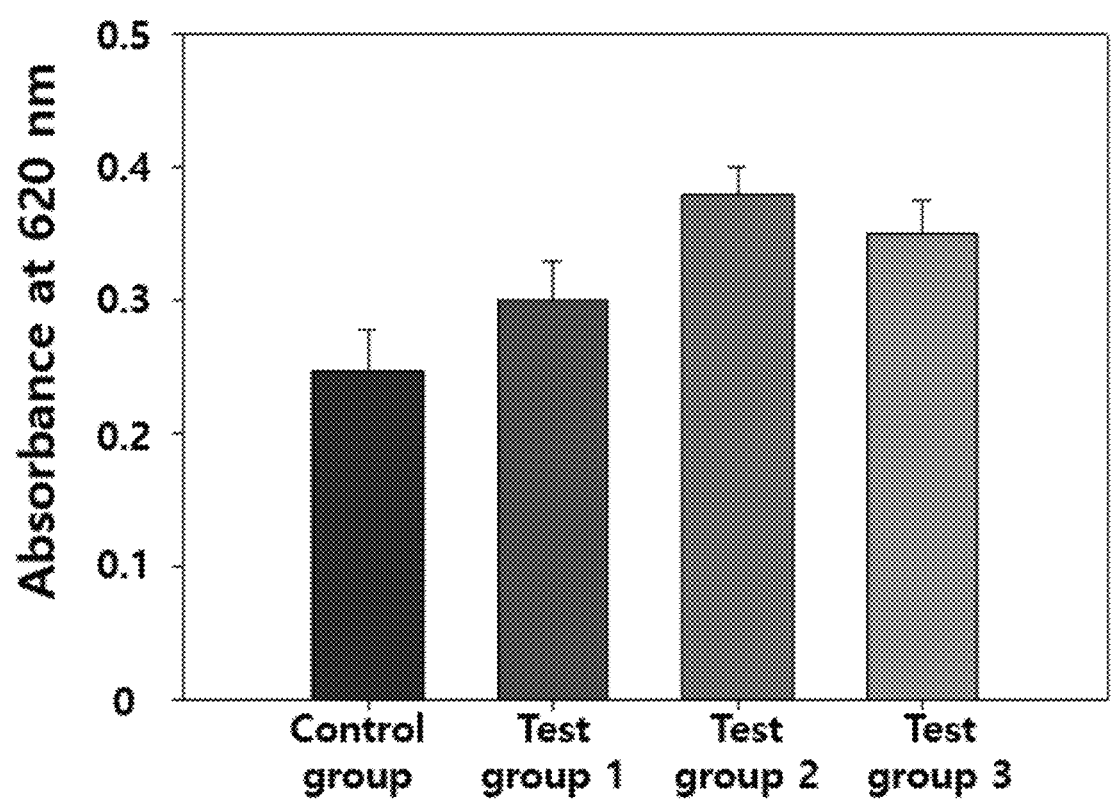
FIG. 5 shows a comparison of binding ability with mucin in respective coating conditions using silk fibroin and cellulose.

The results are shown FIG. 5.

As shown in FIG. 5, it was verified that the mucin binding ability was increased in the order of the control group, test group 1, test group 3, and test group 2; the mucin binding ability was significantly increased by pre-treatment with silk fibroin; and the mucin binding ability of the lactic acid bacteria co-treated with cellulose and silk fibroin was slightly decreased compared with the mucin binding ability of the lactic acid probiotics coated with the pre-treated silk fibroin.

Test Example 5: Intestinal Epithelial Cell Adhesion Ability of Lactic Acid Bacteria Cells Depending on Coating Method of Silk Fibroin In order investigate the intestinal epithelial cell adhesion ability of the lactic acid probiotics manufactured through silk fibroin coating, the adhesion ability of the lactic acid bacteria was investigated using human colon sarcoma cell line HT-29 cells.

The DMED medium supplemented with 10% fetal calf serum (FCS) and antibiotics (100 U/ml penicillin and 100 U/ml streptomycin) was used as a medium for culturing HT-29 cell line. HT-29 cells forming a monolayer in the medium were washed with PBS buffer, and dispensed at $5 \times 10^8$ cells/ml in the 6-well plates. The respective lactic acid probiotics were suspended in PBS to a concentration of 1×10⁹/ml, seeded in the well plates, and then cultured with HT-29 cells for 2 hours in conditions of $CO_2$ 5% and 37° C. After the culture, the non-adhering lactic acid bacteria were removed by washing with PBS five times, and then treated with 0.05% trypsin-0.02% EDTA for 2 minutes to separate HT-29 cells and the lactic acid bacteria adhering to the well plates. The separated cells were diluted to a decimal scale using dilution water, and cultured in MRS or BL agar plates, and then the viable cell count was measured (Trends. Food. Sci. Technol., 1999, Vol. 10, pp 405-410; and Korean Soc. Food. Sci. Nutr., 2016, Vol. 45, pp 12-19).

The epithelial cell adhesion rate was calculated using the following equation.

$$\text{Intestin adhesion rate (\%)} = \frac{\text{Adhering cell count } (CFU)}{\text{Initial viable cell count in suspension } (CFU)} \times 100$$

Additionally, in order to visually investigate the adhesion degree between the intestinal epithelial cells and lactic acid bacteria cells, the lactic acid bacteria cells were fluorescent-stained using the LIVE/DEAD® BacLight™ Bacteial Viability kit, and then observed by an optical microscope.

Figure 6:
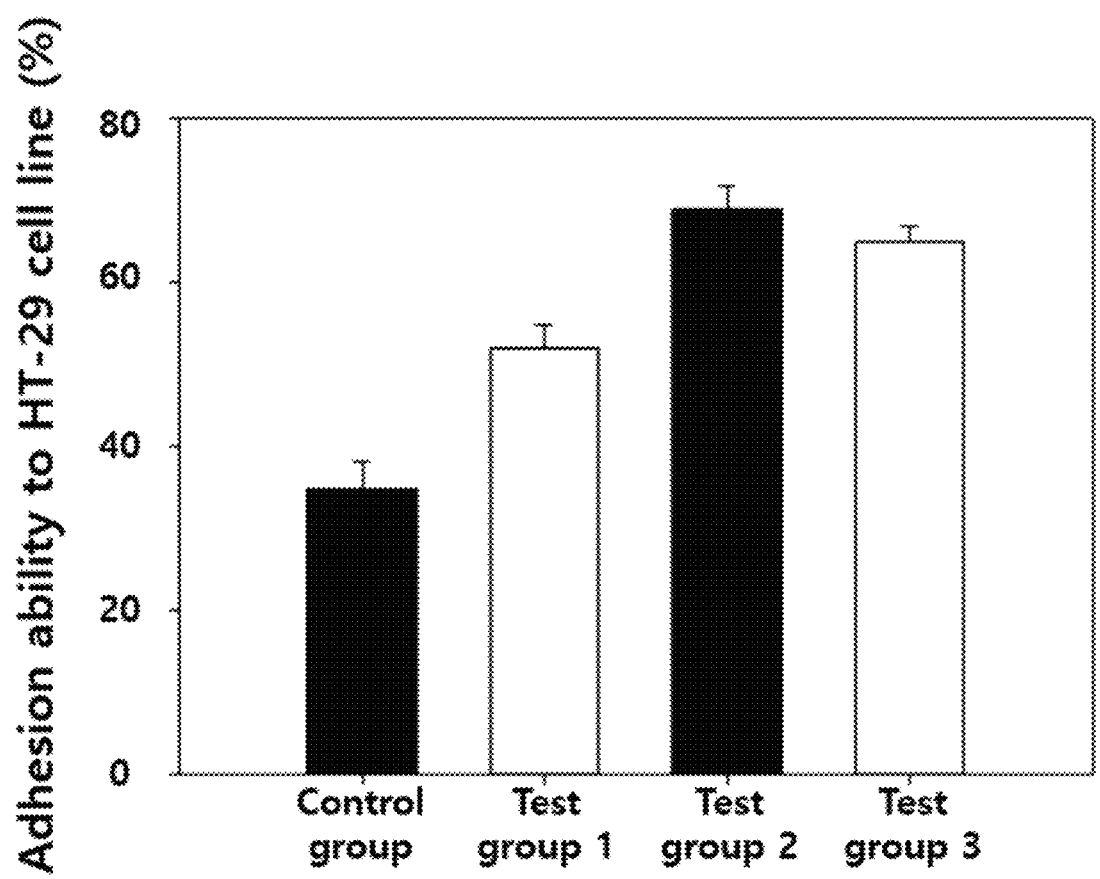
FIG. 6 shows a comparison of binding ability with intestinal epithelial cells (HT-29) in respective coating conditions using silk fibroin and cellulose.

The results of intestinal epithelial cell adhesion rate are shown in FIG. 6.

As shown in FIG. 6, it was investigated that the adhesion ability to HT-29 cell line was increased in the coating with silk fibroin compared with the control group, and further increased in the coating with pre-treated silk fibroin. However, it was verified that the binding ability to HT-29 cells was slightly reduced in the lactic acid probiotics co-coated with pre-treated silk fibroin and cellulose together compared with the lactic acid probiotics manufactured by coating with pre-treated silk fibroin.

Test Example 6: Intestine Tract Environment Stability of Lactic Acid Bacteria Cells Depending on Coating Method of Silk Fibroin In order to evaluate the intestine tract environment stability of the lactic acid probiotics depending on the coating method of silk fibroin, the resistance against acid and resistance against bile of the probiotic powder materials were tested.

In order to determine the resistance against acid, the probiotics were exposed to artificial gastric liquid conditions of pH 2.5 and pH 2.0, and then the vial cell count was analyzed. Specifically, the artificial gastric liquid conditions were adjusted to final pH 2.0 and pH 2.5 by using the artificial gastric liquid conditions on the food disintegration test (2.0 g of sodium chloride, 24.0 ml/L dilute hydrochloric acid, pH 1.2), and then the probiotic powder was added at a concentration of 10% and then exposed. Considering gastric contraction, the reciprocating motion was performed 100 times per minute using the dancing machine equipment (BMS Co., Ltd.) so that the probiotics were exposed to conditions similar to the gastric tract environment, and the exposure time was set to 2 hours considering the gastric passage time. The test groups exposed to the artificial gastric liquid conditions were readjusted to pH 7.0, and then analyzed by an ordinary viable cell count measurement method.

Meanwhile, for the determination of resistance against bile, a medium prepared by filtering 0.5% bile acid and aseptically adding the bile acid was used, and a probiotic powder was added to a concentration of 10%, followed by incubation for 2 hours, and then the viable cell count was measured by an ordinary method.

The results are shown in Table 5 (viability in intestine tract environment (%) depending on coating method of lactic acid bacteria).

TABLE 5

| Strain | Lactic acid bacteria coating method | Resistance against acid Artificial gastric liquid, pH 2.0 | Resistance against acid Artificial gastric liquid, pH 2.5 | Resistance against bile Artificial intestine liquid (0.5% oxigall) |
|---|---|---|---|---|
| E. faecium CKDB003 | Uncoated | 38 | 49 | 41 |
|  | Test group 1 | 42 | 62 | 62 |
|  | Test group 2 | 51 | 73 | 65 |
|  | Test group 3 | 78 | 92 | 72 |
| S. thermophilus CKDB021 | Uncoated | 18 | 24 | 32 |
|  | Test group 1 | 43 | 59 | 38 |
|  | Test group 2 | 58 | 73 | 50 |
|  | Test group 3 | 72 | 88 | 53 |
| B. lactis CKDB005 | Uncoated | 34 | 45 | 47 |
|  | Test group 1 | 58 | 53 | 65 |
|  | Test group 2 | 64 | 73 | 78 |
|  | Test group 3 | 81 | 94 | 73 |
| B. bifidum CKDB001 | Uncoated | 30 | 41 | 46 |
|  | Test group 1 | 46 | 58 | 58 |
|  | Test group 2 | 48 | 61 | 64 |
|  | Test group 3 | 61 | 72 | 65 |
| L. acidophilus CKDB007 | Uncoated | 34 | 38 | 60 |
|  | Test group 1 | 42 | 61 | 68 |
|  | Test group 2 | 58 | 75 | 78 |
|  | Test group 3 | 79 | 94 | 75 |

As shown in Table 5, it was investigated that the resistance against acid and the resistance against bile of the lactic acid probiotics were increased overall by coating lactic acid bacteria with fermented ethanol-pre-treated silk fibroin. It was verified that in the pH 2.0 condition, all the *S. thermophilus* CKDB021, *B. bifidum* CKDB001, *E. faecium* CKDB003, *B. lactis* CKDB005, and *L. acidophilus* CKDB007 strains showed an increase effect in the resistance against acid by at least two-fold in test group 3 compared with the uncoated group. In artificial intestine liquid conditions, the resistance against bile also tended to increase overall by silk fibroin coating, and the *B. lactis* CKDB005 and *L. acidophilus* CKDB007 strains showed the most excellent viability when coated in the conditions of test group 2. It was therefore verified that the resistance against acid or the resistance against bile of the lactic acid probiotics was significantly increased when the lactic acid bacteria were coated with silk fibroin or fermented ethanol-pre-treated silk fibroin or co-coated with such silk fibroin and cellulose.

Test Example 7: Storage Stability of Lactic Acid Bacteria Cells Depending on Coating Method of Silk Fibroin In lactic acid probiotics, at least a certain count of viable cells need to be maintained and preserved during a distribution period of from 12 months to 24 months.

In general, diplococcus type lactic acid bacteria, such as *Enterococcus*-based, for example, *E. faecium* and *E. faecalis*, show high stability when exposed to high-temperature and high-humidity conditions, but most of the lactic acid bacteria show a significantly decreased trend in stability when exposed to high temperature and humidity conditions.

In the present invention, in order to investigate the storage stability of the lactic acid probiotics, the lactic acid probiotics were subdivided into a polyethylene bag (inner) and an aluminum bag (outer) in 50 g each, and stored in severe conditions (4500, 75% humidity), and the samples were collected in each storage time to check the viable cell count.

The results are shown in Table 6 (storage stability (%) depending on coating method of lactic acid bacteria).

TABLE 6

| Silk fibroin | Lactic acid bacteria coating method | Severe conditions (40° C., 75%) Viability by storage period (%) | | |
|---|---|---|---|---|
| | | 4 weeks | 8 weeks | 12 weeks |
| E.faecium CKDB003 | Control group | 76 | 52 | 43 |
| | Test group 1 | 92 | 81 | 72 |
| | Test group 2 | 96 | 92 | 89 |
| | Test group 3 | 99 | 96 | 95 |
| S.thermophilus CKDB021 | Control group | 42 | 33 | 20 |
| | Test group 1 | 48 | 40 | 27 |
| | Test group 2 | 62 | 51 | 48 |
| | Test group 3 | 83 | 72 | 68 |
| B.lactis CKDB005 | Control group | 27 | 21 | 18 |
| | Test group 1 | 53 | 48 | 45 |
| | Test group 2 | 96 | 95 | 95 |
| | Test group 3 | 99 | 96 | 95 |
| B.bifidum CKDB001 | Control group | 20 | 18 | 16 |
| | Test group 1 | 34 | 28 | 20 |
| | Test group 2 | 61 | 55 | 52 |
| | Test group 3 | 89 | 72 | 54 |
| L.acidophilus CKDB007 | Control group | 18 | 18 | 15 |
| | Test group 1 | 43 | 38 | 38 |
| | Test group 2 | 85 | 78 | 77 |
| | Test group 3 | 92 | 90 | 85 |

As shown in Table 6, it was verified that *B. lactis, E. faecium*, and *L. acidophilus* strains showed significantly increased stability in severe conditions through coating using silk fibroin, and besides, *B. bifidum* and *S. thermophilus* stains also showed slightly improved stability in severe conditions.

[Accession Numbers]
Depository institution name: Korea Research Institute of Bioscience and Biotechnology
Accession number: KCTC13114BP
Deposit date: 2016.09.23
Depository institution name: Korea Research Institute of Bioscience and Biotechnology
Accession number: KCTC13115BP
Deposit date: 2016.09.23
Depository institution name: Korea Research Institute of Bioscience and Biotechnology
Accession number: KCTC13116BP
Deposit date: 2016.09.23
Depository institution name: Korea Research Institute of Bioscience and Biotechnology
Accession number: KCTC13117BP
Deposit date: 2016.09.23
Depository institution name: Korea Research Institute of Bioscience and Biotechnology
Accession number: KCTC13118BP
Deposit date: 2016.09.23

What is claimed is:

1. A composition comprising lactic acid bacteria coated with silk fibroin.

2. The composition of claim 1, wherein the lactic acid bacteria are coated with silk fibroin and cellulose.

3. The composition of claim 1, wherein the silk fibroin is pre-treated with ethanol.

4. The composition of claim 3, wherein the ethanol has a concentration of 85% (v/v) or more.

5. The composition of claim 1, wherein the lactic acid bacteria are selected from the group consisting of the genera *Lactobacillus, Lactococcus, Enterococcus, Streptococcus*, and *Bifidobacterium*.

6. The composition of claim 5, wherein the lactic acid bacteria are selected from the group consisting of *Lactobacillus acidophilus, Lactobacillus plantarum, Lactobacillus delbrueckii* ssp. *bulgaricus, Lactococcus lactis, Enterococcus faecium, Enterococcus faecalis, Streptococcus thermophilus, Bifidobacterium bifidum*, and *Bifidobacterium lactis*.

7. The composition of claim 6, wherein the lactic acid bacteria are selected from the group consisting of *Lactobacillus acidophilus* CKDB007 (Accession No.: KCTC13117BP), *Enterococcus faecium* CKDB003 (Accession No.: KCTC13115BP), *Streptococcus thermophilus* CKDB021 (Accession No.: KCTC13118BP), *Bifidobacterium bifidum* CKDB001 (Accession No.: KCTC13114BP), and *Bifidobacterium lactis* CKDB005 (Accession No.: KCTC13116BP).

8. The composition of claim 1, wherein the composition is selected from the group consisting of a food composition, a probiotic composition, a pharmaceutical composition, and a feed composition.

* * * * *